Oct. 13, 1959 G. MERRILL Plant Pat. 1,872
PEACH TREE
Filed July 21, 1958
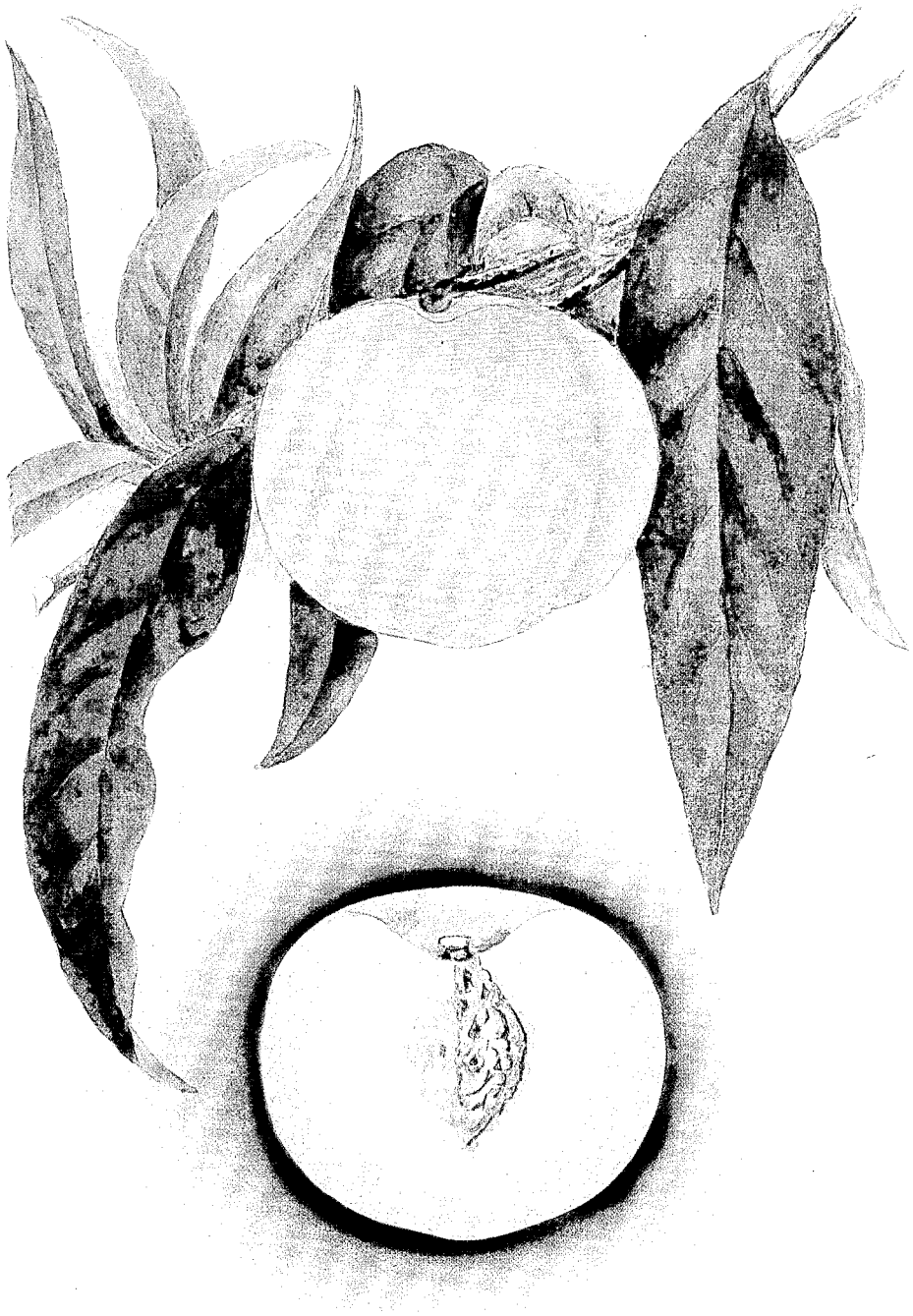
WITNESS
Addison E. Avery
INVENTOR
Irwin Merrill
HUEBNER & WORREL
BY Richard M. Worrel
ATTY.

United States Patent Office

Plant Pat. 1,872

Patented Oct. 13, 1959

1,872

PEACH TREE

Grant Merrill, Red Bluff, Calif.

Application July 21, 1958, Serial No. 750,055

1 Claim. (Cl. 47—62)

This invention relates to a new and distinct variety of peach tree which is highly productive and which bears large, highly colored, yellow fleshed, firm freestone peaches of good shipping quality.

A distinguishing characteristic of the instant variety is that it ripens about four days after Redhaven (unpatented) and about three weeks after Merrill Gemfree (Plant Patent No. 1,409), and has a very red skin color when firm ripe. The fruit of the present variety is distinguished from the Merrill Gemfree (Plant Patent No. 1,409) which it most nearly resembles by being almost completely freestone when allowed to soften off the tree and by ripening about three weeks later than said Gemfree.

I originated the instant variety of fruit on my farm near Red Bluff, Tehama County, California, in the following manner:

Seeds were planted for four generations of open pollinated blossoms ($F_4$) starting with J. H. Hale (unpatented) and selecting each time for high color, firmness and size of fruit along with good tree producing characteristics. In the fourth generation ($F_4$) this new variety was selected.

In the fall of 1956, several trees planted the previous year were budded to this selection on my farm at Red Bluff, Tehama County, California, and the trees fruited in July 1958. The fruit and tree characteristics proved identical to those of the original seedlings. Also several trees of Merrill June (Plant Patent No. 869) were grafted in the spring of 1956 to this selection at our farm near Lamont, Kern County, California. These trees fruited in June 1958 and proved to be identical with the original seedling.

The drawing consists of a water color painting of two twigs of the instant variety peach tree having characteristic foliage represented thereon and a mature peach borne by one of the twigs. A characteristic peach is also shown as it appears at maturity divided on its suture plane to reveal flesh coloration and one-half of a pit. One half of the pit has been removed for illustration of pit-well coloration while the other half of the pit remains for illustrative convenience.

Referring now more specifically to the pomological details of this new and distinct variety of peach tree, the following is an outline description thereof; all major color plate identifications being by reference to Maerz and Paul Dictionary of Color:

*Tree*

Medium size, medium vigorous, moderately upright, medium dense, vase formed by pruning, productive, regular bearer.

Trunk: Medium stocky, medium smooth.

Branches: Grey on older branches, reddish brown on younger branches. Lenticels—medium numerous, medium large.

Leaves: (Selected from midportion of vigorous unbranched terminal shoot 18" to 24" long).

*Length.*—6⅝" to 7⅝", average 7⅛".

*Width.*—1 5/16" to 1 7/16", average 1⅜".

*Size.*—Medium.

*Shape.*—Lanceolate, tip acuminate.

*Thickness.*—Medium.

*Color.*—Upper surface green (22–L–7), lighter green on lower surface (22–J–6). Heavy midrib a lighter green (19–K–2).

*Class* (Meader and Blake: Proceedings Am. Soc. Hor. Sc., vol. 27, page 206).—Mostly 2, some 3. Width—length ratio, average .19. Apex angle—22½° to 26½°, average 24°. Base angle—66° to 78°, average 70°.

*Margin.*—Glandular, crenate.

*Petiole.*—Medium length, medium thickness.

*Glands.*—Reniform, one to seven, average four, medium size, position, on petiole and base of leaf.

*Stipules.*—At base of leaf dropping off early.

Flower buds: Medium size, medium length, truncate to obtuse, plump, free, pubescent, pollen moderately abundant.

Flowers: Medium late compared with other varieties, small size, salmon pink in color.

*Fruit*

Maturity when described, eating ripe.

Size: Variable.

*Axial diameter.*—2⅝" to 2⅞", average 2¾".

*Transverse in suture plane.*—2¾" to 3 1/16", average 2 15/16".

*At right angles to suture plane.*—2⅝" to 2 13/16", average 2¾".

Form: Mostly globose, some slightly ovate, some slightly obovate.

*Suture.*—Distinct, shallow, extends from base to beyond, but discontinuous at apex, has slight depression beyond pistil point.

*Ventral surface.*—Rounded, lips equal to unequal.

*Cavity.*—Elongated in suture plane, with suture showing on both sides. Depth ½" to ⅝", average 9/16". Breadth ⅜" to ⅝", average ½". Markings—yellow to yellowish green, red blush extends into cavity on most.

*Base.*—Truncate.

*Apex.*—Mostly rounded, some slightly depressed.

*Pistil point.*—Apical.

*Stem.*—Length average ½". Diameter ⅛", adheres to stone frequently.

*Skin.*—Relatively thick, tough. Free when soft ripe, tendency to crack—none. Color—almost entire fruit covered with red blush, obscuring undercolor almost entirely. (9–L–7) to (1–L–12) to (4–L–6) to extremely dark (6–L–6). Down—scant, short, seldom rolls up when rubbed.

Flesh: Color near stone (9–L–2) to (9–L–7) in the center of the flesh, with some red in the flesh near the skin (1–J–11). There occasionally is some green in the flesh, next to pit on the dorsal side.

*Amygadalin.*—Scant.

*Juice.*—Moderate.

*Texture.*—Firm, fine.

*Fibers.*—Fine, few, tender.

*Ripens.*—Slightly unevenly, ripening first on the suture side.

*Flavor.*—Subacid, delicate.

*Aroma.*—Distinct.

*Eating quality.*—Good.

Stone: Free, over entire surface when soft ripe. Adheres to flesh along ventral edge, especially near apex on some, when firm ripe. Fibers medium length.

*Size.*—Medium length 1⅜" to 1½", average 1 7/16".

Breadth 1 3/32" to 1 5/16", average 1 3/16". Thickness 3/4" to 7/8", average 13/16".

*Form.*—Obovate.

*Base.*—Straight.

*Apex.*—Cuspidate.

*Hilum.*—Oval.

*Sides.*—Mostly unequal, rounded toward apex, flattened toward base.

*Surface.*—Irregularly furrowed and pitted throughout. Ridges—pronounced along dorsal edge, interrupted usually one or more times, pits circular and elongated. Dorsal edge—usually two ridges interrupted one or more times, discontinuous near apex. Ventral edge—thick with many small furrows.

*Color.*—Tan (11–C–6). Some red on both edges on many.

*Tendency to split.*—None.

Use: Market, local, dessert, culinary, long distance shipping.

Keeping quality: Good.

It is to be understood that normal variations in the described characteristics of the new variety peach tree must be expected to result from environmental changes, such as in climatic and soil conditions, and from changes in cultural practices, such as in pruning, thinning, fertilizing, spraying, irrigating, and the like. The description is that of the variety produced under the ecological conditions prevailing at my farm at Red Bluff, Tehama County, California and the characteristics are found to hold true in asexual reproduction of the variety.

Having described and illustrated my invention, what I claim as new and desire to secure by Letters Patent is:

A new and distinct variety of peach tree substantially as described and illustrated, characterized as to novelty by the very red skin of the fruit while firm ripe, ripening about four days after Redhaven (unpatented) and about three weeks after Merrill Gemfree (Plant Patent No. 1,409), being similar to said Merrill Gemfree but being an improvement on that variety in its later ripening period and in the flesh being almost completely free from the stone when allowed to soften off of the tree.

No references cited.